United States Patent
Fujii et al.

(10) Patent No.: US 9,063,077 B2
(45) Date of Patent: Jun. 23, 2015

(54) ANALYSIS TOOL AND MANUFACTURING METHOD THEREOF

(71) Applicant: ARKRAY Inc., Kyoto (JP)

(72) Inventors: Tomohiro Fujii, Kyoto (JP); Yasuhide Kusaka, Kyoto (JP)

(73) Assignee: Arkray, Inc., Kyoto (JP)

(*) Notice: Subject to any disclaimer, the term of this patent is extended or adjusted under 35 U.S.C. 154(b) by 0 days.

(21) Appl. No.: 14/195,994

(22) Filed: Mar. 4, 2014

(65) Prior Publication Data

US 2014/0186548 A1 Jul. 3, 2014

Related U.S. Application Data

(62) Division of application No. 12/740,834, filed as application No. PCT/JP2008/069981 on Oct. 31, 2008, now abandoned.

(30) Foreign Application Priority Data

Oct. 31, 2007 (JP) .................................. 2007-282781

(51) Int. Cl.
*G01N 27/327* (2006.01)
*B05D 5/12* (2006.01)
*B32B 38/04* (2006.01)

(52) U.S. Cl.
CPC .............. *G01N 27/3271* (2013.01); *B05D 5/12* (2013.01); *B32B 38/04* (2013.01); *G01N 27/3272* (2013.01)

(58) Field of Classification Search
CPC ......... G01N 27/327; B05D 5/12; B32B 38/04

USPC ................... 204/400–403.15; 427/554, 77; 422/82.01, 68.1; 435/287.1
See application file for complete search history.

(56) References Cited

U.S. PATENT DOCUMENTS

| | | | |
|---|---|---|---|
| 2003/0175946 A1 | 9/2003 | Tokunaga et al. |
| 2006/0188395 A1 | 8/2006 | Taniike et al. |
| 2009/0120806 A1 | 5/2009 | Onoda et al. |

FOREIGN PATENT DOCUMENTS

| CN | 1262739 | | 8/2000 |
|---|---|---|---|
| EP | 1 615 031 | A1 | 1/2006 |
| JP | 9-189675 | | 7/1997 |
| JP | 10-318969 | | 12/1998 |
| JP | 2001-516038 | | 9/2001 |
| JP | 2007-510902 | | 4/2007 |
| WO | 00/42422 | A1 | 7/2000 |
| WO | 2005/075979 | | 8/2005 |
| WO | 2007/026683 | | 3/2007 |
| WO | 2008/040997 | | 4/2008 |
| WO | WO 2008/040997 | * | 4/2008 |

OTHER PUBLICATIONS

Extended European Search Report dated Oct. 29, 2014 issued in corresponding European Application No. 08845459.0, 5 pages.

* cited by examiner

*Primary Examiner* — Jennifer Dieterle
(74) *Attorney, Agent, or Firm* — Thomas | Horstemeyer, LLP

(57) ABSTRACT

This aims to provide an analyzing tool including a substrate, a first electrode formed on the substrate and having an action pole, a second electrode formed on the substrate and having an opposed pole, and a first regulating element for regulating such a contact area in the action pole as to contact a specimen. The analyzing tool further comprises second regulating elements for regulating the effective area for electron transfers in at least one of the action pole and the opposed pole.

16 Claims, 15 Drawing Sheets

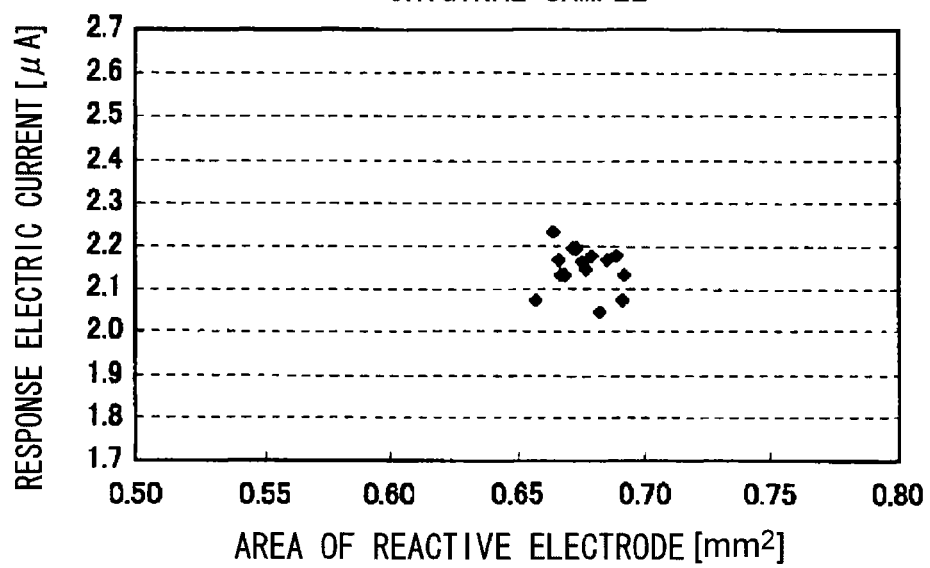
FIG.15A ORIGINAL SAMPLE
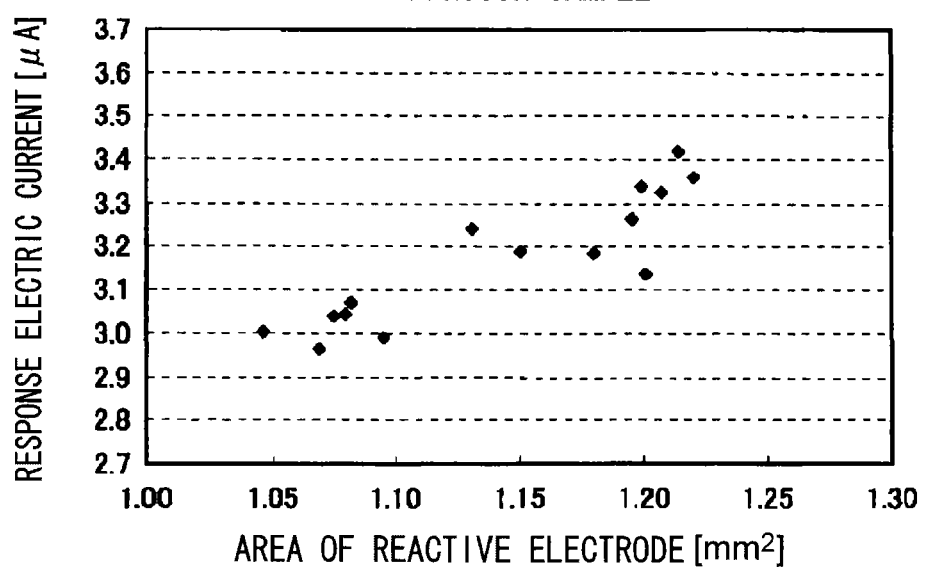
FIG.15B COMPARISON SAMPLE

ANALYSIS TOOL AND MANUFACTURING METHOD THEREOF

CROSS REFERENCE TO RELATED APPLICATION

This is a Divisional Application of copending U.S. patent application having Ser. No.: 12/740,834, filed on Apr. 30, 2010, and entitled "ANALYSIS TOOL AND MANUFACTURING METHOD THEREOF," which is the National Phase of International Application No. PCT/JP2008/069981, filed 31 Oct. 2008, which claims priority to and the benefit of JP patent application number 2007-282781, filed 31 Oct. 2007, the contents of all which are incorporated by reference herein.

TECHNICAL FIELD

The present invention relates to a method of manufacturing an analysis tool used to analyze certain components (for example, glucose, cholesterol, or lactic acid) of a specimen (for example, a biochemical specimen such as blood or urine).

BACKGROUND ART

When the glucose concentration in blood is measured, a method of using a disposable analysis tool is being employed as a simple and easy technique. The analysis tool includes, for example, an electrode-type biosensor 6 shown in FIG. 16 hereto (see, for example, Japanese Patent Application Laid-Open (JP-A) No. 10-318969). The biosensor 6 is configured such that a response electric current value necessary to calculate a blood-sugar level is measured using electrodes 61 and 62 provided on a substrate 60. The electrodes 61 and 62 are covered by an insulating film 64 having an opening 64A, and the portions of the electrodes 61 and 62 exposed by the opening 64A constitute a reactive electrode 61A and an counter electrode 62A.

In the biosensor 6, the area of the reactive electrode 61A or the counter electrode 62A is controlled by the opening 64A of the insulating film 64. In other words, it is necessary to form the insulating film 64 using, for example, photolithography in order to control the area of the reactive electrode 61A or the counter electrode 62A. In addition, a deviation may be generated in the area of the reactive electrode 61A due to a deviation in the dimension of the opening 64A between plural glucose sensors 6. The reactive electrode 61A facilitates transfer of electrons from/to analysis target components, and a deviation in the area of the reactive electrode 61A generates a deviation in the sensitivity of the biosensor 6.

As a method of controlling an electrode area of the analysis tool, there is the following method as well.

In the chemical sensor electrode 7 shown in FIG. 17 hereto, a narrow-width neck section 71 extends from an electrode main body section 70, and the electrode main body section 70 is exposed by the opening 73 of the insulating film 72 (see, for example, Japanese Patent Application Laid-Open (JP-A) No. 2007-510902). The edge of the opening 73 in the insulating film 72 traverses the neck section 71. Therefore, even when the dimension of the opening 73 has a deviation, it is possible to suppress a deviation in the area of the electrode main body section 70.

The electrode strip 8 shown in FIG. 18 hereto has an reactive electrode 80 and a dummy electrode 81. The electrodes 80 and 81 are exposed by the opening 83 of the insulating film 82 (see, for example, Japanese Patent Application Laid-Open (JP-A) No. 2001-516038). In such an electrode strip 8, since the reactive electrode 80 and the dummy electrode 81 have an island shape, it is possible to prevent the deviation in the area of the reactive electrode 80 even when the deviation exists in the dimension of the opening 83.

On the contrary, in the chemical sensor electrode 7 or the electrode strip 8 shown in FIGS. 17 and 18, it is necessary to form the insulating films 72 and 82 using, for example, photolithography or the like in order to control the area of the electrode main body section 70 or the reactive electrode 80. Therefore, processes or equipments for manufacturing the analysis tools 7 and 8 become complicated, and manufacturing cost increases.

In the biosensor 9 shown in FIGS. 19A and 19B hereto, a slit 91 is formed in a metal film of the substrate 90, and the reactive electrode 93 and the counter electrode 94 are controlled by a pair of covers 92 (see, for example, Japanese Patent Application Laid-Open (JP-A) No. 9-189675). In this biosensor 9, since the area of the reactive electrode 93 can be controlled without the insulating film, it is possible to advantageously make it easier to perform the manufacturing processes. On the other hand, since the area of the reactive electrode 93 depends on the accuracy of positioning or the shape of a pair of covers 92, it is difficult to accurately control the area of the reactive electrode 93.

DISCLOSURE OF THE INVENTION

Problems to be Solved by the Invention

The present invention has been made to control the area of the reactive electrode of the electrode-type analysis tool in a simple, easy, and accurate manner.

Means of Solving the Problems

According to a first aspect of the present invention, there is provided an analysis tool including: a substrate; a first electrode which is formed on the substrate and has an reactive electrode; a second electrode which is formed on the substrate and has an counter electrode; a first control element for controlling a contact area making contact with a specimen in the reactive electrode; and a second control element for controlling an effective area for performing transfer of electrons in at least one of the reactive electrode and the counter electrode.

For example, the second control element is provided to control the effective area for performing transfer of electrons in the reactive electrode. For example, the second control element is at least a slit. For example, the slit has a main line extending in a first direction where the reactive electrode and counter electrode are lined up and a subsidiary line extending in a second direction intersecting with the first direction.

It is preferable that the first control element is arranged such that the edge for controlling the contact area traverses the subsidiary line.

According to a second aspect of the invention, there is provided a method of manufacturing an analysis tool, the method including: a first process for forming plural electrodes on a mother substrate; a second process for forming an element for defining an effective area for performing transfer of electrons in the reactive electrode; and a third process for defining a contact area making contact with a specimen in the reactive electrode.

For example, the second process is performed by forming a slit in an electrode including the reactive electrode. For example, the slit is formed by irradiating laser light onto the electrode. For example, the slit is formed to have a main line extending in a first direction where the reactive electrode and the counter electrode are lined up and a subsidiary line extending in a second direction intersecting with the first direction.

For example, the third process is performed by arranging a control element on the mother substrate. The control element is arranged such that an edge for controlling the contact area traverses the subsidiary line.

For example, the first process is performed by irradiating laser light onto the conductive layer after a conductive layer is formed on the mother substrate.

BRIEF DESCRIPTION OF THE DRAWINGS

FIGS. 15A and 15B are graphs illustrating measurement results of the area of the reactive electrode and the response electric current according to the second embodiment.

BEST MODE FOR CARRYING OUT THE INVENTION

Hereinafter, the analysis tool and the method of manufacturing the same according to the present invention is described below by exemplifying a biosensor with reference to the accompanying drawings.

First, the first embodiment of the present invention will be described with reference to FIGS. 1 to 10.

Figure 1:
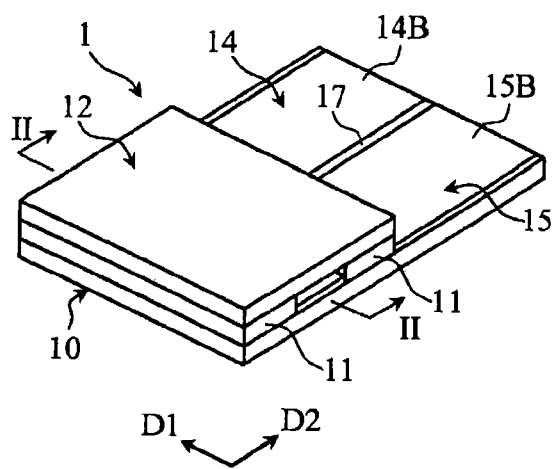
FIG. 1 is a perspective diagram illustrating the entire biosensor as an example of the analysis tool according to a first embodiment of the present invention.
Figure 2:
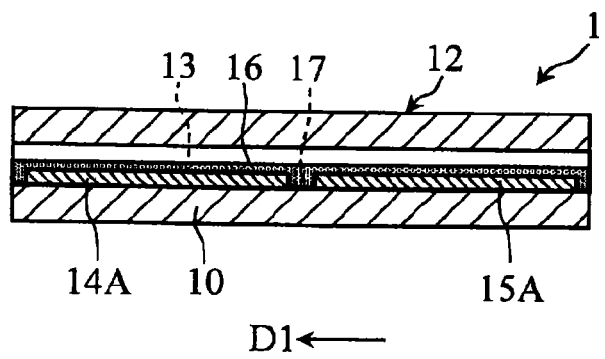
FIG. 2 is a cross-sectional view along the line Il-Il of FIG. 1.
Figure 3:
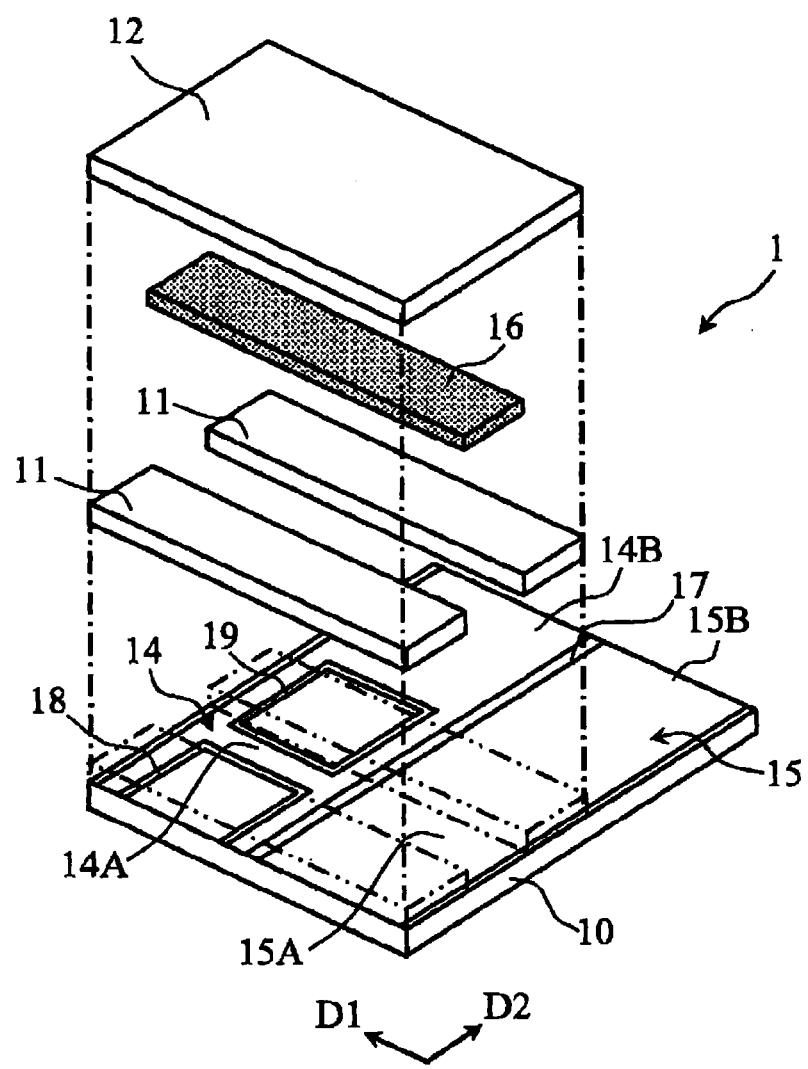
FIG. 3 is an exploded perspective view illustrating the biosensor of FIG. 1.

The biosensor 1 shown in FIGS. 1 to 3 is constructed as a disposable device, and is installed in an analyzer (not shown) such as a concentration measurement apparatus and used to analyze a certain component (for example, glucose, cholesterol, or lactic acid) within a specimen (for example, a biochemical specimen such as blood or urine). The biosensor 1 has a configuration obtained by bonding the cover 12 to the substrate 10 having an approximately long rectangular shape by interposing a pair of spacers 11 therebetween. In the biosensor 1, a capillary 13 extending in the width direction D1 of the substrate 10 is defined by each element 10 to 12.

The substrate 10 is formed in a shape larger than the cover 12 using an insulation resin material such as PET. The substrate 10 has a protrusion in a lateral direction of the cover 12. On the surface of the substrate 10, electrodes 14 and 15 and a reagent layer 16 are provided.

Figure 4:
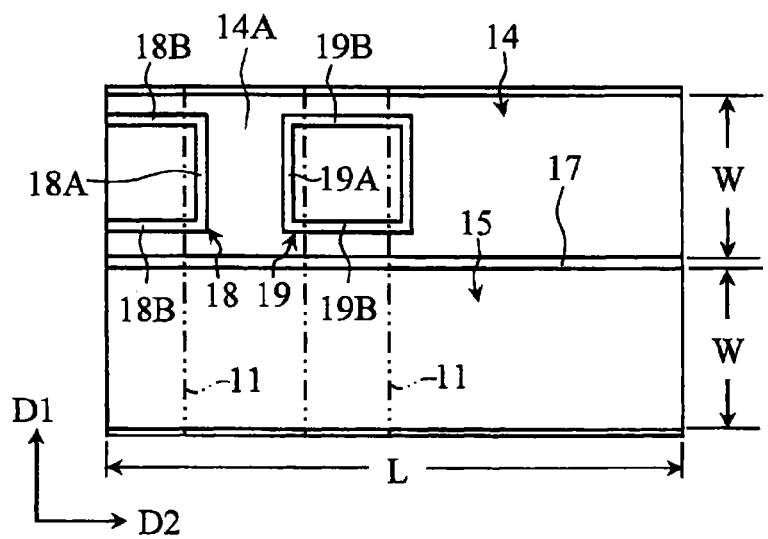
FIG. 4 is a top plan view illustrating the biosensor of FIG. 1 by removing the spacer, the reagent layer, and the cover.

The electrodes 14 and 15 are formed to have a band shape extending in the longitudinal direction D2 of the substrate 10 such that, for example, the length L is 2 to 50 mm (refer to FIG. 4), and the width W is 0.1 to 5 mm (refer to FIG. 4). The electrodes 14 and 15 have exposed electrode portions (including the reactive electrode 14A and the counter electrode 15A) and terminal portions 14B and 15B.

The reactive electrode 14A and the counter electrode 15A are exposed portions inside the capillary 13 and separated from each other by the slit 17. The width of the slit 17 is set to, for example, 10 to 300 μm. The reactive electrode 14A and the counter electrode 15A make contact with the specimen introduced into the capillary 13. Here, the reactive electrode 14A performs transfer of electrons from/to analysis target components within the specimen, and the area of the reactive electrode 14A influences the measurement accuracy of the biosensor 1.

As shown in FIGS. 3 and 4, the electrode 14 further includes slits 18 and 19. These slits 18 and 19 are provided to define an effective area, and include main lines 18A and 19A, and subsidiary lines 18B and 19B. Here, the effective area of the reactive electrode 14A means the area of the portion for performing transfer of electrons from/to the analysis target components within the specimen. In other words, the reactive electrode 14A has a smaller effective area which is an area for performing transfer of electrons from/to analysis target components within the specimen by providing slits 18 and 19 in comparison with the area making contact with the specimen inside the capillary 13. Here, the area of the reactive electrode 14A substantially contributing to such transfer of electrons is referred to as an effective area.

The main lines 18A and 19A extend in a direction of D1, and their lengths are set to, for example, 50 to 98% of the widths W of the electrodes 14 and 15. The distance between the main lines 18A and 19A is set to, for example, 30% to 98% of the distance between a pair of the spacers 11. On the other hand, the subsidiary lines 18B and 19B extend in the direction of D2. The slit 18 has a U-shape, and the slit 19 has a rectangular shape.

As shown in FIGS. 1 to 3, the terminal portions 14B and 15B are provided to make contact with a connector (not shown) of the analyzer when the biosensor 1 is installed in the analyzer.

The reagent layer 16 is to cover the reactive electrode 14A and the counter electrode 15A in series inside the capillary 13. The reagent layer 16 includes, for example, an oxidoreductase and an electron carrier material, and is formed in a solid state readily dissolved in the specimen such as blood.

The oxidoreductase is selected depending on the type of the analysis target component within the specimen. For example, when glucose is analyzed, glucose oxidase (GOD) or glucose dehydrogenase (GDH) may be used, and typically, PQQGDH is used. The electron carrier material may include, for example, a ruthenium complex or an iron complex, and typically [Ru(NH$_3$)$_6$]Cl$_3$ or K$_3$[Fe(CN)$_6$].

A pair of spacers 11 are to define the distance from the surface of the substrate 10 to the lower surface of the cover 12, i.e., the height of the capillary 13, and are configured of, for example, a double-face adhesive tape or a hot-melt film. These spaces 11 extend in the width direction of the substrate 10 and are also arranged to be separated in a longitudinal direction of the substrate 10. In other words, a pair of spacers 11 define the width of the capillary 13 and the area (the contact area making contact with the specimen) of the portion exposed within the capillary 13 (the reactive electrode 14A and the counter electrode 15A) in the electrodes 14 and 15.

The cover 12 is provided to define the capillary 13 in association with the spacers 11 or the like. The cover 12 is formed of the same material as that of the substrate 10 such as PET or thermoplastic resin having a high wettability such as vinylon or high-crystalline PVA.

The capillary 13 is provided to move the introduced specimen such as blood in the width direction of the substrate 10 using a capillary action and retain the introduced specimen. In other words, in the capillary 13, when the specimen is introduced, the specimen moves while discharging gas within the capillary 13. In this case, inside the capillary 13, the reagent layer 16 is dissolved so as to provide a liquid-phase reaction system including analysis target components such as an oxidoreductase, an electron carrier material, and glucose.

Next, a method of manufacturing the biosensor 1 will be described with reference to FIGS. 5 to 10.

Figure 5:
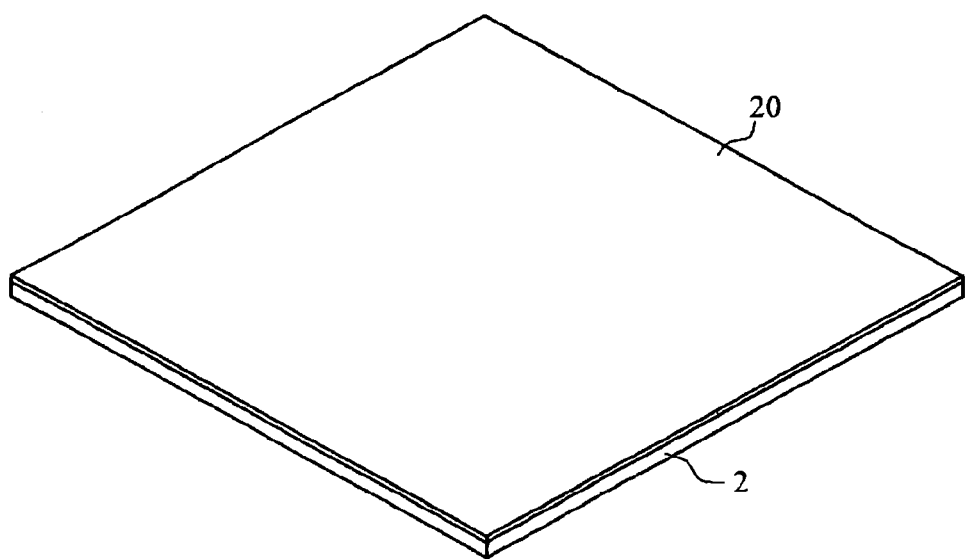
FIG. 5 is a perspective diagram for describing a method of manufacturing the biosensor of FIG. 1.

First, as shown in FIG. 5, a conductive layer 20 is formed on the surface of the mother substrate 2. The conductive layer 20 is formed of, for example, gold, platinum, palladium, nickel, or carbon and has a thickness of 0.001 to 100 μm. The formation of the conductive layer 20 is performed by, for example, screen printing, CVD, sputtering, or deposition.

Figure 6A:
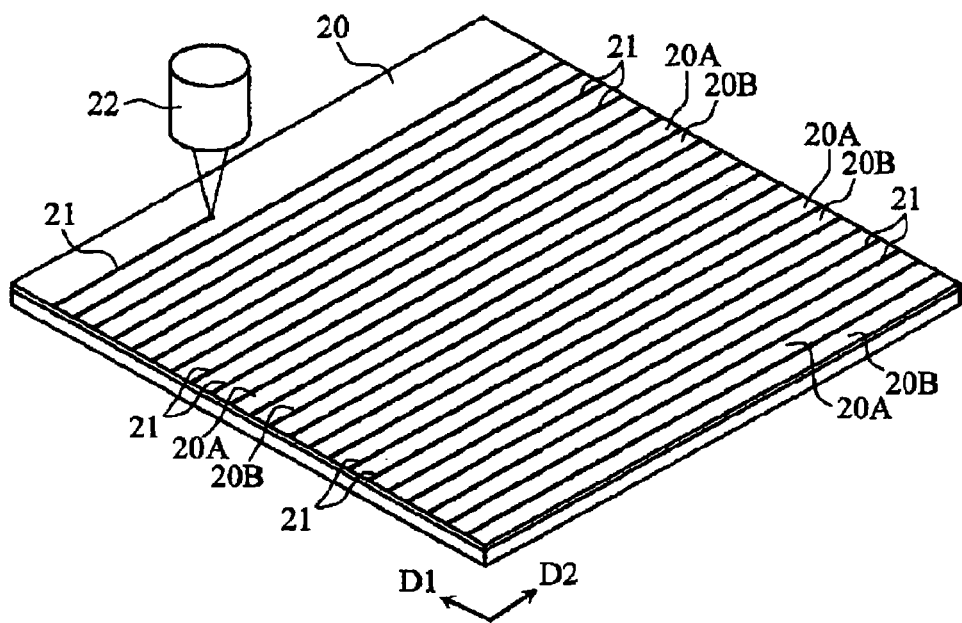
FIG. 6A is a perspective diagram for describing a method of manufacturing the biosensor of FIG. 1.
Figure 6B:
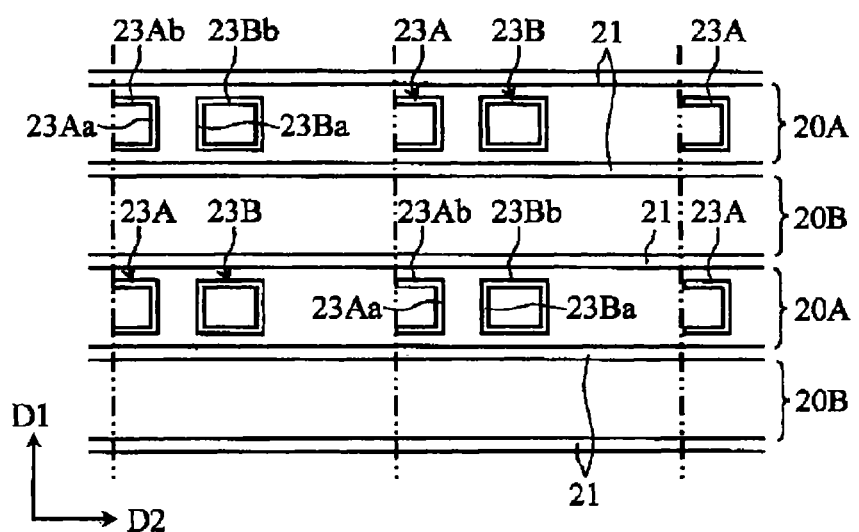
FIG. 6B is a top plan view illustrating main components of FIG. 6A.

Next, as shown in FIGS. 6A and 6B, plural separation slits 21 extending in a direction of D2 are formed on the conductive layer 20. As a result, the conductive layer 20 has plural band-shape electrodes 20A and 20B insulated from each other. These slits 21 are formed to have a width of 10 to 300 μm by scanning laser light along a predetermined path, for example, using a laser oscillator 22. The laser oscillator 22 may include, for example, a CO$_2$ laser oscillator or a YAG laser oscillator, capable of oscillating laser light having a wavelength that can be easily absorbed by the conductive layer 20 and hardly absorbed by the mother substrate 2.

Meanwhile, a process of forming the conductive layer 20 and a process of forming the slits 21 are not necessarily performed in a separate manner, but may be performed in a collective manner, for example, using a predetermined mask by simultaneously forming the conductive layer 20 and the slits 21 to provide plural band-shape electrodes 20A and 20B.

Next, as shown in FIG. 6B, slits 23A and 23B for controlling an effective area of the reactive electrode 14A are formed. Such slits 23A and 23B are formed to have main lines 23Aa and 23Ba and subsidiary lines 23Ab and 23Bb, for example, using a laser oscillator 22. The main lines 23Aa and 23Ba extend in a direction of D1, and have a length corresponding to, for example, 50 to 98% of the widths of band-shape electrodes 20A and 20B. The distance between the main lines 23Aa and 23Ba is set to, for example, 30 to 98% of the distance between a pair of spacers 24A and 24B which will be described below. On the other hand, the subsidiary lines 23Ab and 23Bb extend in a direction of D2, in which the slit 23A has a U-shape as a whole, and the slit 23B has a rectangular shape as a whole. Of course, the shapes of the slits 23A and 23B may be variously changed, for example, such that the slit 23A has a rectangular shape, and the slit 23B has a U-shape. Alternatively, both of the slits 23A and 23B may have a U-shape, or both of the slits 23A and 23B may have a rectangular shape.

Figure 7A:
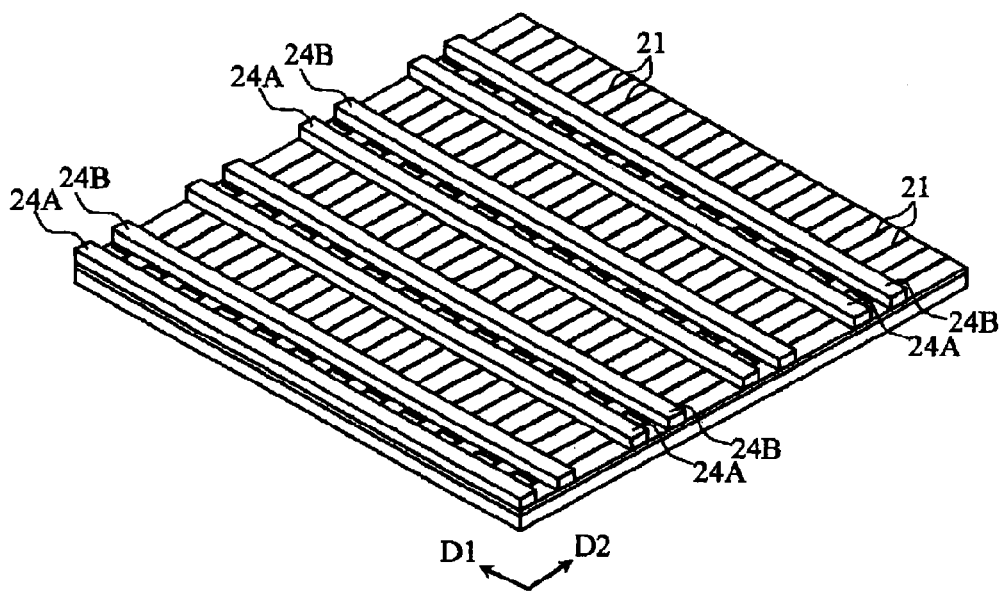
FIGS. 7A and 7B are top plan views for describing a method of manufacturing the biosensor of FIG. 1.
Figure 7B:
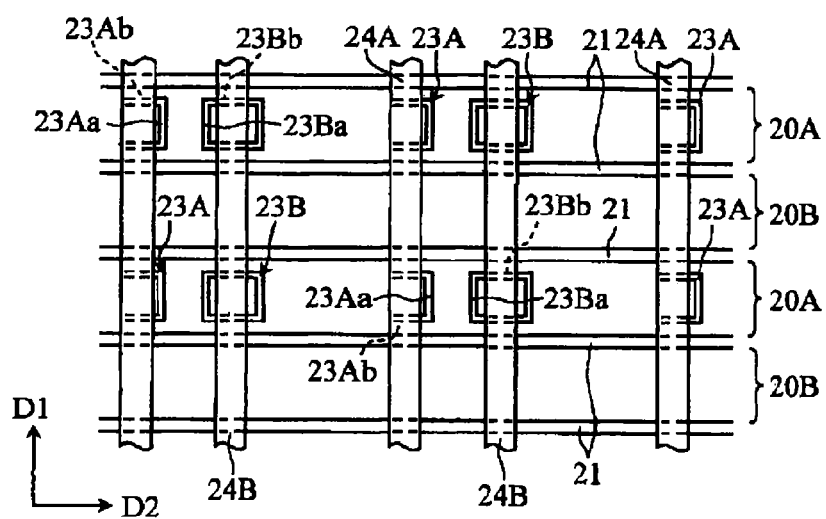

Next, as shown in FIGS. 7A and 7B, plural spacers 24A and 24B are attached to extend in a direction of D1 perpendicular to plural separation slits 21. Such spacers 24A and 24B may be attached farther than the distance between the main lines 23Aa and 23Ba such that the main lines 23Aa and 23Ba of the slits 23A and 23B for controlling the effective area of the reactive electrode 14A are exposed. In other words, the spacers 24A and 24B are arranged such that edges of the spacers 24A and 24B traverse the subsidiary lines 23Ab and 23Bb of the slits 23A and 23B.

The spacers 24A and 24B may include, for example, a double-face adhesive tape or a hot-melt film. The width and the thickness of each of the spacers 24A and 24B are set to, for example, 1 to 20 mm and 20 to 300 μm, respectively. The distance between the spacers 24A and 24B is set to, for example, 100 to 3000 μm.

Figure 8A:
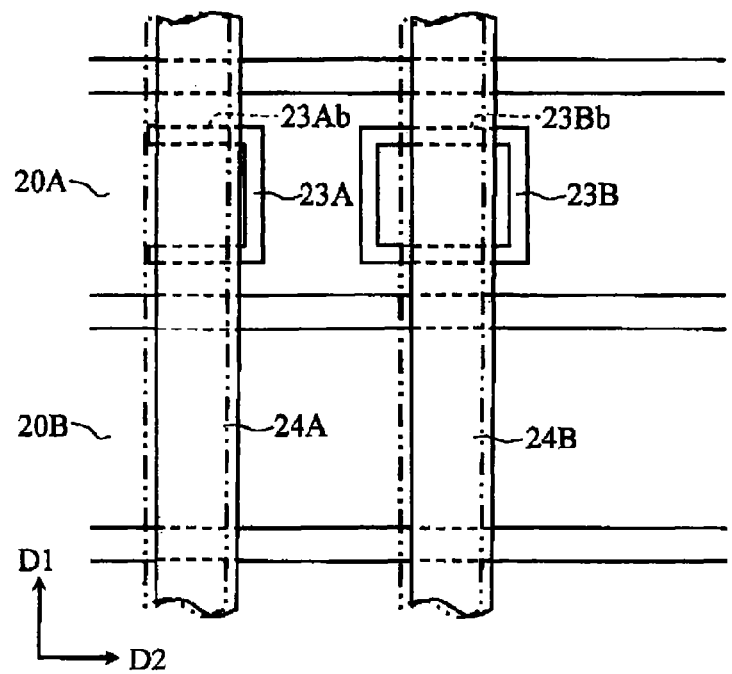
FIGS. 8A and 8B are top plan views for describing effects of the method of manufacturing the biosensor according to the present invention by enlarging main components of FIG. 7B.
Figure 8B:
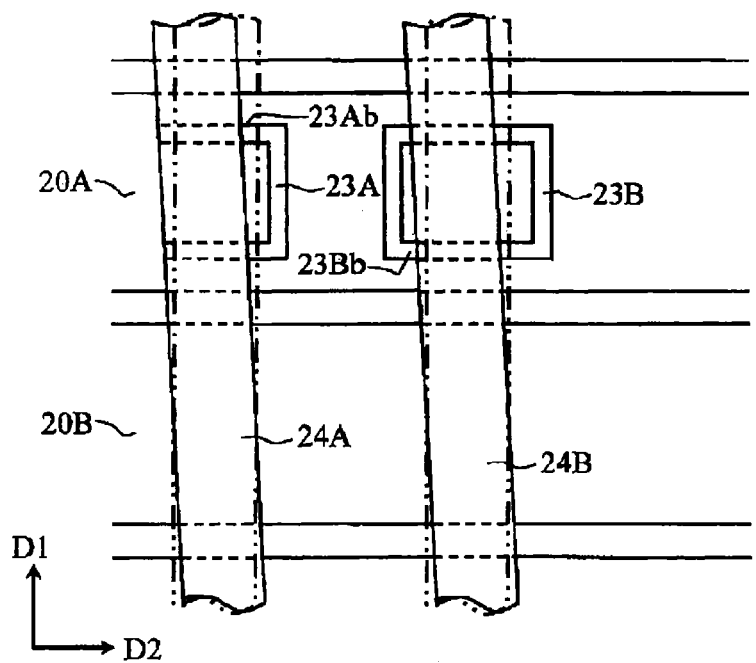

As shown in FIG. 8A, even when the positions where the spacers 24A and 24B are attached are deviated from the target positions in a direction of D2, or the spacers 24A and 24B are attached with an inclination as shown in FIG. 8B, it is possible to suppress a deviation of the effective area of the reactive electrode 14A as long as edges of the spacers 24A and 24B are arranged to traverse the subsidiary lines 23Ab and 23Bb of the slits 23A and 23B. In other words, even when the edges of the spacers 24A and 24B are deviated from predetermined positions in a portion having a narrow width on the electron transfer surface contributing to transfer of electrons in the reactive electrode 14, it is possible to reduce a variation of the (effective) area of the electron transfer surface. Therefore, it is possible to improve the measurement accuracy by reducing a variation of the area of the reactive electrode 14 influencing the measurement accuracy of the biosensor 1. In addition, even when positions of a pair of spacers 24A and 24B are deviated from predetermined positions, if the distance between a pair of spacers 24A and 24B is within an allowable range, it is possible to compensate for a variation in the effective area caused by a positional deviation of the spacer 24A and a variation in the effective area caused by a positional deviation of the spacer 24B. As a result, it is possible to reduce a variation in the area (effective area) of the electron transfer surface, and in this regard, it is possible to improve the measurement accuracy of the biosensor 1.

Figure 9A:
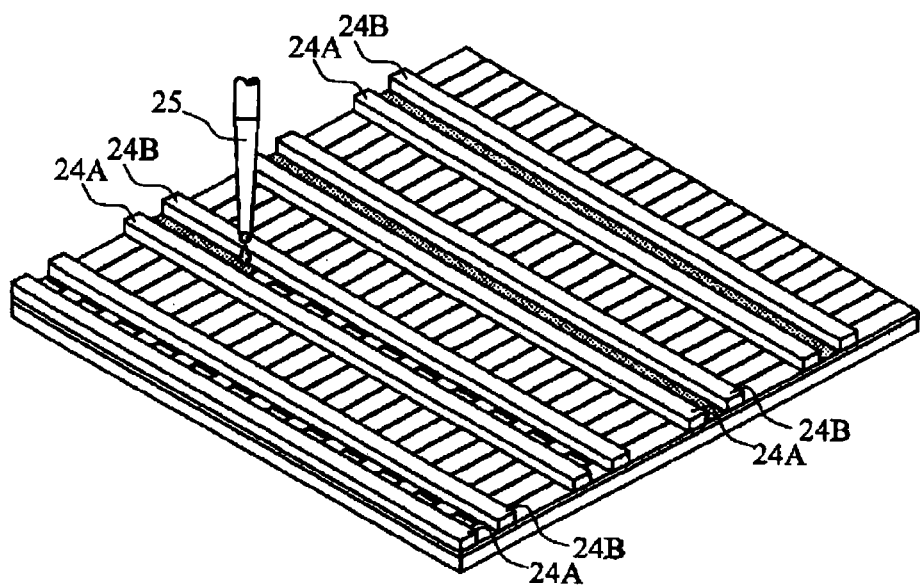
FIGS. 9A and 9B are perspective diagrams for describing a method of manufacturing the biosensor of FIG. 1.
Figure 9B:
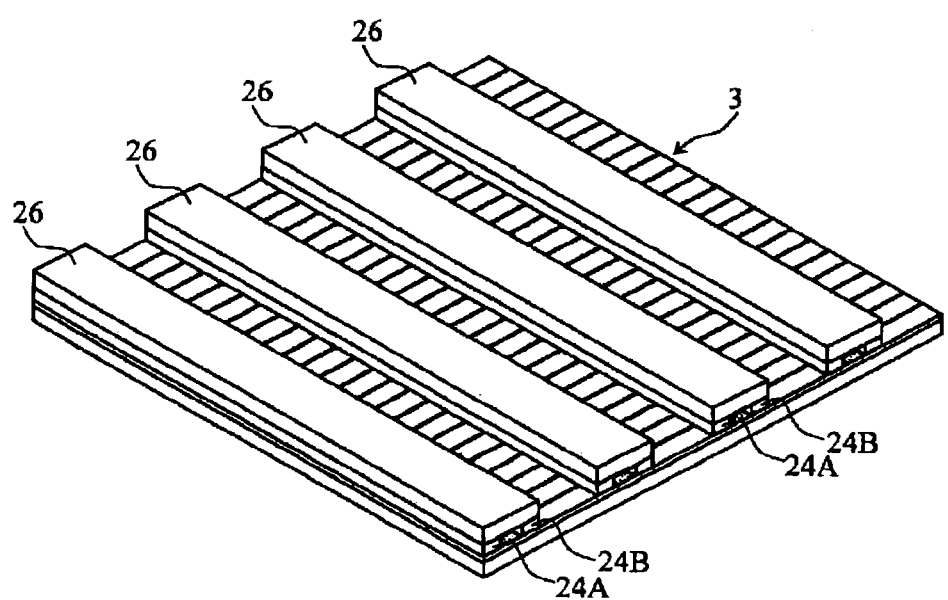
Figure 10:
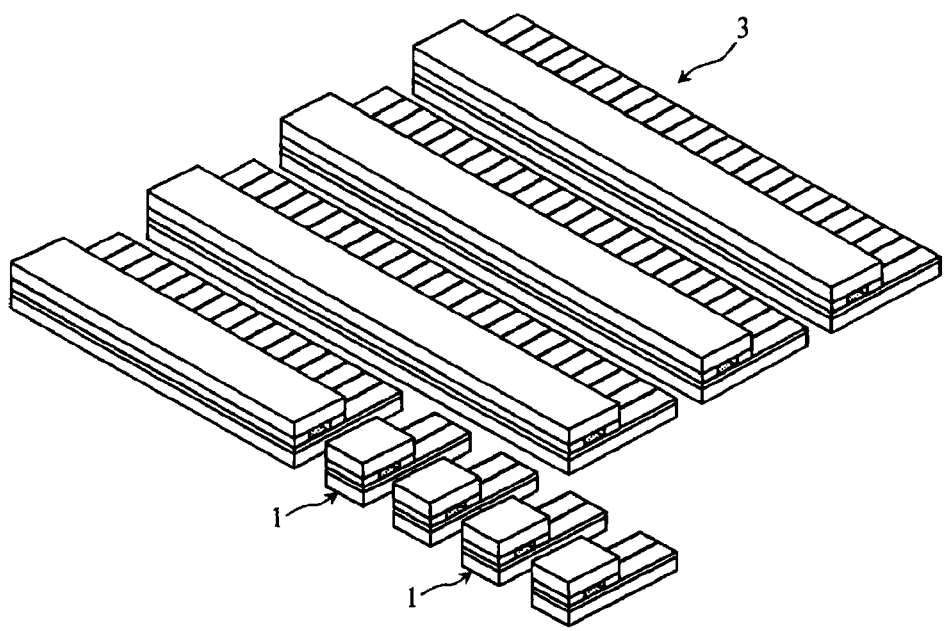
FIG. 10 is a perspective diagram for describing effects of the method of manufacturing the biosensor according to the present invention.

Next, as shown in FIG. 9A, a reagent solution is applied between the spacers 24A and 24B, for example, using a dispenser 25 known in the art. A reagent solution includes a liquid-phase or slurry-phase material containing an oxidoreductase and an electron carrier material. The oxidoreductase is selected depending on the type of the analysis target component within the specimen. For example, when a biosensor 1 appropriate to analyze glucose is formed, glucose oxidase (GOD) or glucose dehydrogenase (GDH) is used. The electron carrier material includes, for example, a ruthenium complex or an iron complex, and typically, [Ru(NH$_3$)$_6$]Cl$_3$ or K$_3$[Fe(CN)$_6$].

Next, as shown in FIG. 9A, a sensor assembly 3 is obtained by attaching the cover 26 so as to bridge the spacers 24A and 24B. The cover 26 may be formed of, for example, the same material as that of the mother substrate 2 such as thermoplastic resin or PET having a high wettability such as vinylon or high-crystalline PVA.

Finally, plural biosensors 1 can be obtained by cutting the sensor assembly 3 along a predetermined cutting line. The cutting of the sensor assembly 3 is performed using, for example, a diamond cutter.

In the manufacturing method described above, it is possible to obtain a biosensor 1 capable of suppressing a deviation in the area (the effective area) of the electron transfer surface of the reactive electrode 14A. Therefore, it is possible to improve measurement accuracy by suppressing a deviation in the measurement result caused by a deviation in the effective area of the reactive electrode 14A of the biosensor 1.

In addition, since the effective area of the reactive electrode 14A is not controlled by the opening of the insulating layer which covers the electrodes 14 and 15, it is unnecessary to form the insulating layer in order to control the area of the electron transfer surface of the reactive electrode 14A. Therefore, it is possible to control the area of the electron transfer surface of the reactive electrode 14A in a simple, easy, and inexpensive manner without complicating the manufacturing processes or equipments.

In addition, if the slits 23A and 23B, and the laser oscillator 22 are used to control the area of the electron transfer surface of the reactive electrode 14A when plural separation slits 21 are formed in the conductive layer 20 using the laser oscillator 22, it unnecessary to prepare special equipment in order to form the slits 23A and 23B. Therefore, in this regard, it is possible to improve the measurement accuracy of the biosensor 1 by controlling the area of the electrode transfer surface of the reactive electrode 14A in a simple, easy, and inexpensive manner.

Figure 11A:
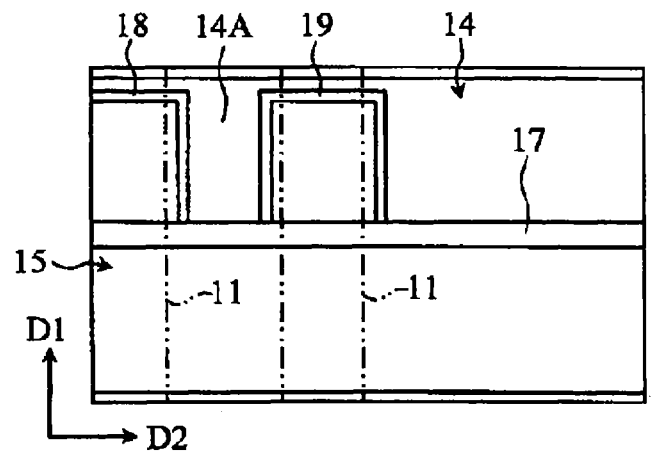
FIGS. 11A-C are top plan views corresponding to FIG. 4 for describing additional examples of the analysis tool according to the present invention.
Figure 11B:
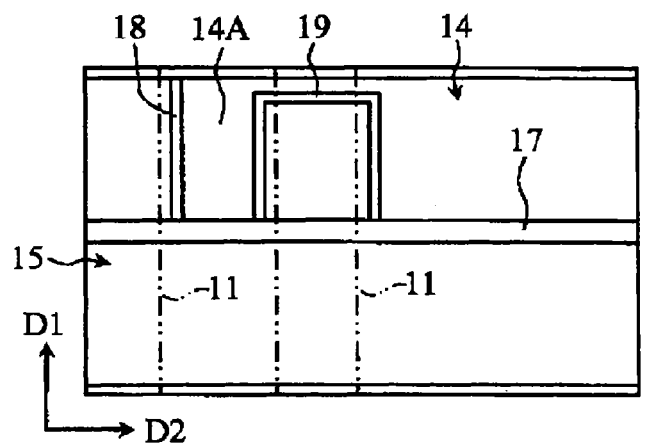
Figure 11C:
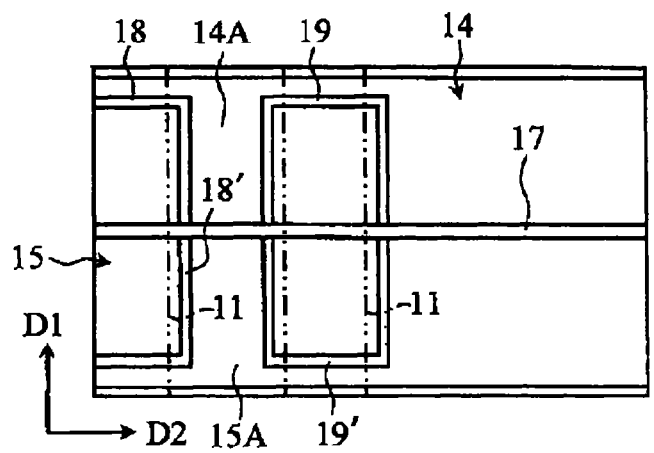

The present invention is not limited to the aforementioned embodiments, but may be modified in various manners, for example, as shown in FIGS. 11A to 11C.

In the example shown in FIG. 11A, the slits 18 and 19 for controlling the effective area of the reactive electrode 14A are formed in an L-shape and a U-shape, respectively, by omitting one of the subsidiary lines in the slits 18 and 19.

In the example shown in FIG. 11B, the slit 18 for controlling the effective area of the reactive electrode 14A is formed in an I-shape by omitting the subsidiary lines, and the slit 19 is formed in a U-shape by omitting one of the subsidiary lines.

In the example shown in FIG. 11C, the slits 18 and 19 for controlling the effective area of the reactive electrode 14A are formed in an L-shape and a U-shape by omitting one of the subsidiary lines and, the slits 18' and 19' are also formed in the counter electrode 15A. The slits 18 and 19 and the slits 18' and 19' are symmetrically arranged with respect to the separation slit 17.

Next, the second embodiment of the present invention will be described with reference to FIGS. 12 to 14.

Figure 12:
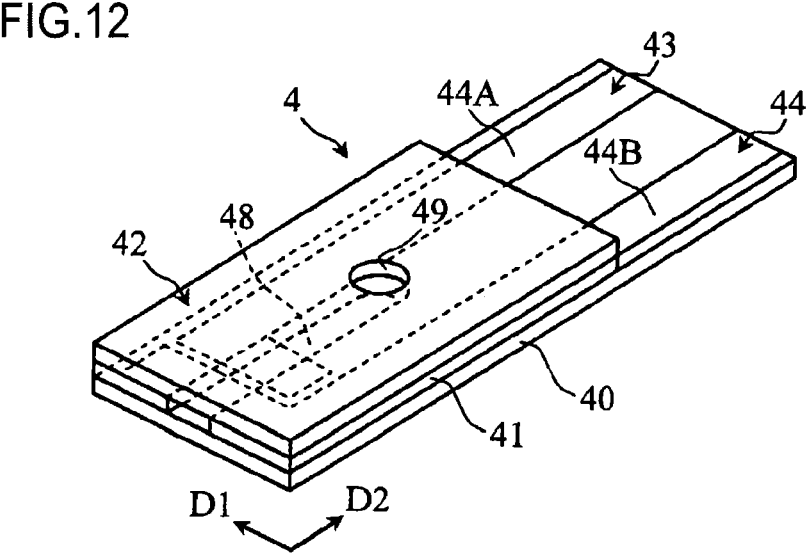
FIG. 12 is a perspective diagram illustrating the entire biosensor as an example of the analysis tool according to the first embodiment of the present invention.
Figure 13:
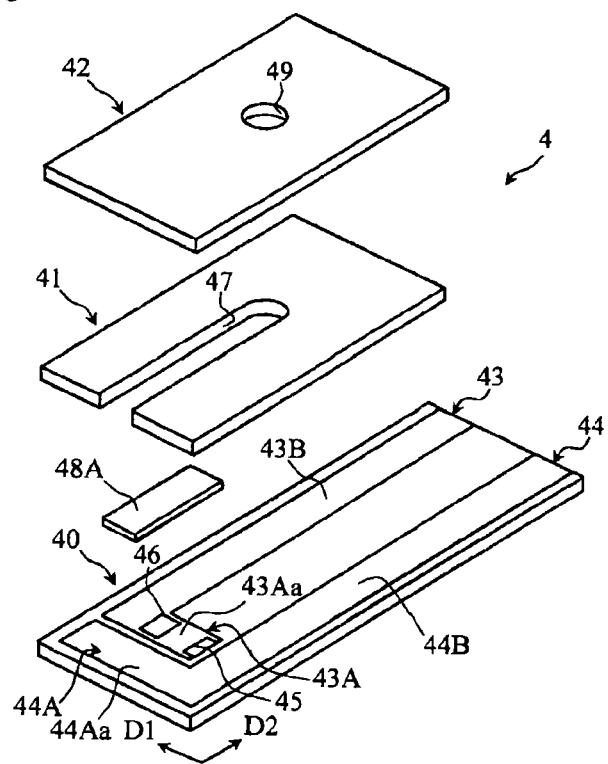
FIG. 13 is an exploded perspective diagram illustrating the biosensor of FIG. 12.
Figure 14:
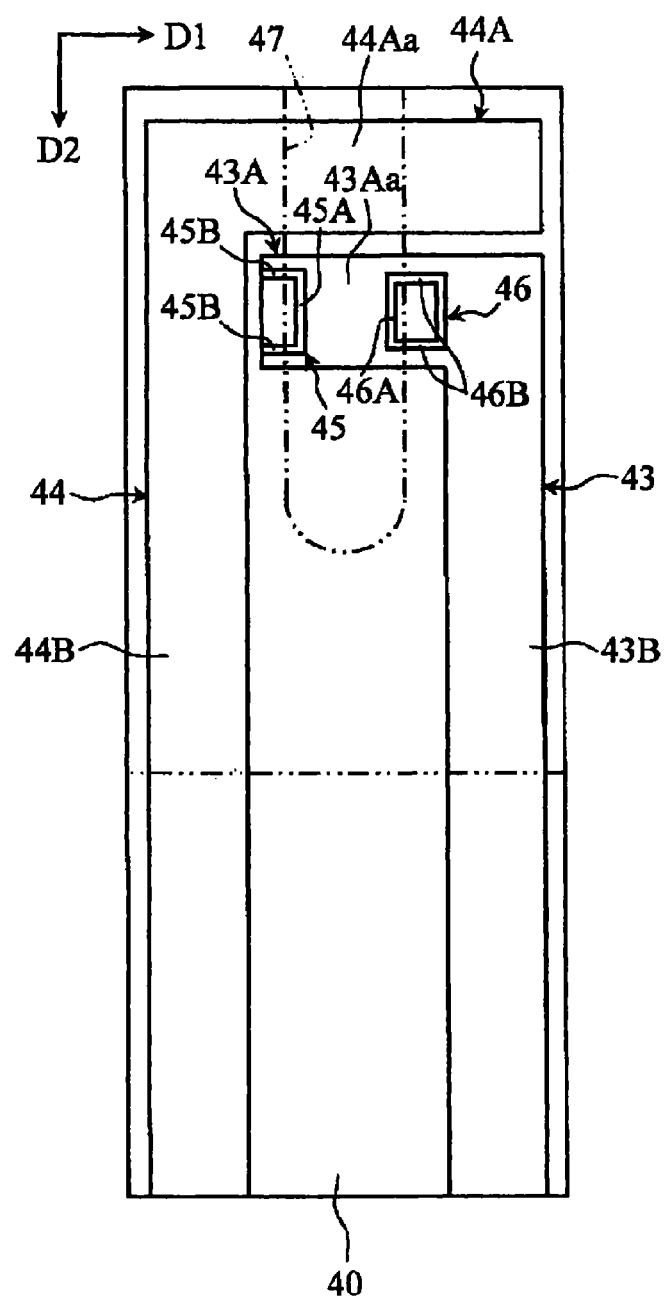
FIG. 14 is a top plan view illustrating the biosensor of FIG. 12 by removing the spacer, the reagent layer, and the cover.
Figure 16:
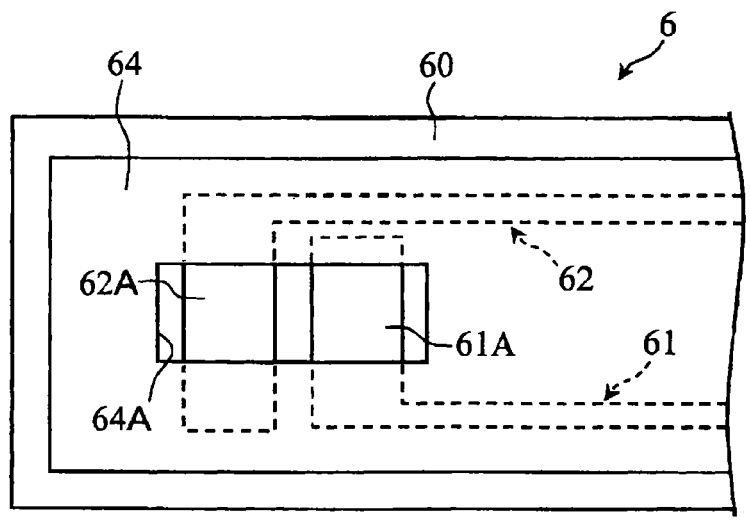
FIG. 16 is a top plan view illustrating main components of the biosensor as an example of the analysis tool of the related art.
Figure 17:
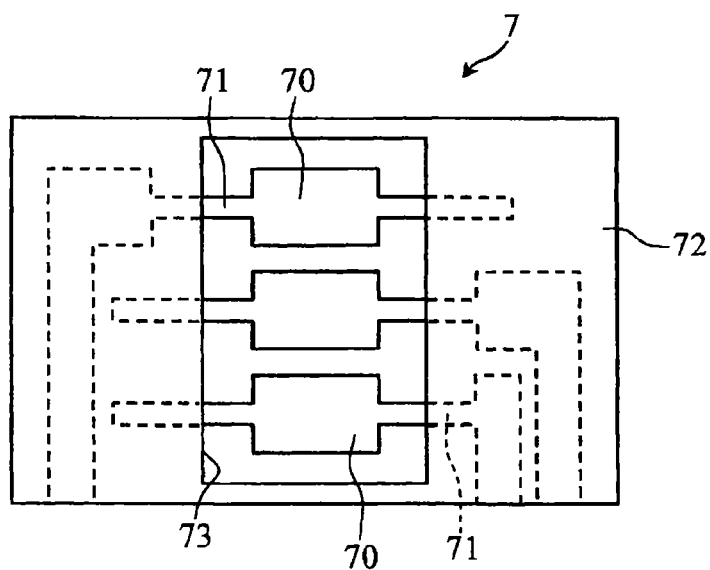
FIG. 17 is a top plan view illustrating a chemical sensor electrode as another example of the analysis tool of the related art.
Figure 18:
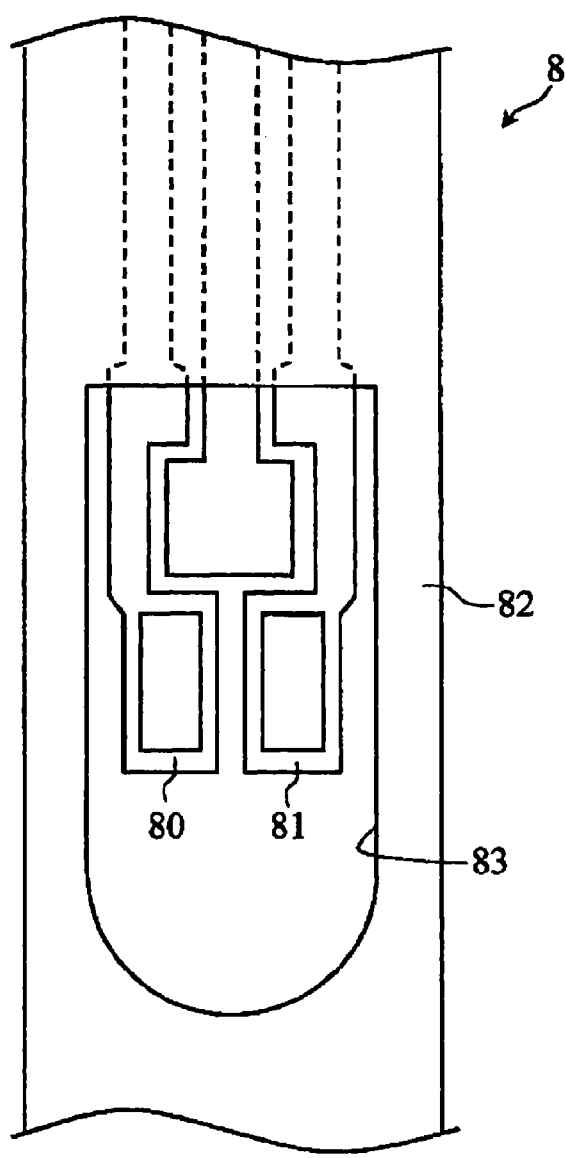
FIG. 18 is a top plan view illustrating main components of the electrode strip as further another example of the analysis tool of the related art.
Figure 19A:
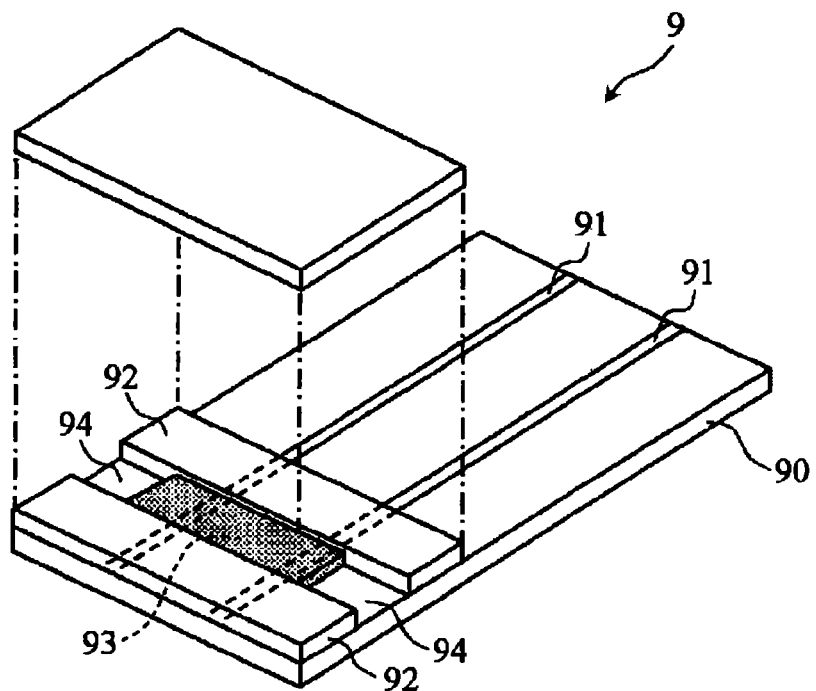
FIG. 19A is a perspective diagram illustrating as still further another example of the analysis tool of the related art by partially exploding the biosensor.
Figure 19B:
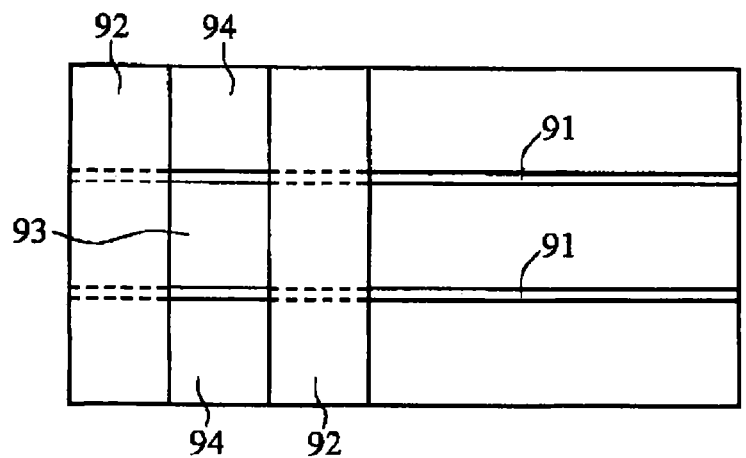
FIG. 19B is a top plan view illustrating the biosensor of FIG. 19A by removing the reagent layer and the cover.

The biosensor 4 shown in FIGS. 12 to 14 is formed by stacking the substrate 40, the spacer 41, and the cover 42 in a similar way to that of the biosensor 1 described above (refer to FIGS. 1 to 3).

Electrodes 43 and 44 are formed on the substrate 40. The electrodes 43 and 44 have bending portions 43A and 44A extending in a direction of D1 and lead portions 43B and 44B extending in a direction of D2. The bending portions 43A and 44A are arranged in parallel in a direction of D2, and include an reactive electrode 43Aa and the counter electrode 44Aa defined by the spacer 41. In addition, slits 45 and 46 are formed in the bending portion 43A. Such slits 45 and 46 are provided to define the area (the effective area) of the electron transfer surface of the reactive electrode 43Aa. Similar to the slits 18 and 19 of the aforementioned biosensor 1 (refer to FIGS. 3 and 4), the slits 45 and 46 include main lines 45A and 46A and subsidiary lines 45B and 46B.

The main lines 45A and 46A extend in a direction of D2, and their lengths are set to, for example, 50 to 98% of the width of the bending portion 43A. The distance between the main lines 45A and 46A is set to, for example, 30 to 98% of the width of the slit in the spacer 41 which will be described below. On the other hand, the subsidiary lines 45B and 46B extend in a direction of D1, the slit 45 is formed in a U-shape, and the slit 46 is formed in a rectangular shape.

The spacer 41 is provided to define the distance from the surface of the substrate 40 to the lower surface of the cover 42, i.e., the height of the capillary 48, and has a slit 47. The slit 47 defines the width of the capillary 48 for introducing the specimen and the area of the portion (the reactive electrode 43Aa and the counter electrode 44Aa) exposed within the capillary 48 in the electrodes 43 and 44. The spacer 41 is arranged such that the edge of the slit 47 extending in a direction of D2 traverses the subsidiary lines 45B and 46B of the slits 45 and 46.

Here, the capillary 48 is provided to move the introduced specimen such as blood in a longitudinal direction D2 of the substrate 40 using a capillary action and maintain the introduced specimen. In the inner side thereof, the reagent layer 48A is formed to cover at least the reactive electrode 43Aa. Such a spacer 41 is configured of, for example, a double-face adhesive tape or a hot-melt film.

The cover 42 is provided to define the capillary 13 in association with the spacer 41 or the like, and has a thru-hole 49. The cover 42 is formed of the same material as that of the substrate 40 such as thermoplastic resin or PET having a high wettability such as vinylon or high-crystalline PVA.

In the biosensor 4, since the effective area of the reactive electrode 43Aa is defined by the slits 45 and 46, a deviation in the area of the reactive electrode 43Aa is suppressed. Therefore, it is possible to suppress a deviation in the sensor sensitivity of the biosensor 4 and perform the concentration measurement with excellent accuracy.

Since the effective area of the reactive electrode 43Aa is not controlled by the opening of the insulating layer that covers the electrodes 44 and 45, it is unnecessary to form the insulating layer in order to control the area of the reactive electrode 43Aa. Therefore, it is possible to control the area of the reactive electrode 43Aa in a simple, easy, and inexpensive manner without complicating the manufacturing processes or equipments.

Meanwhile, the shapes of the slits 45 and 46 or the biosensor 4 may be variously modified as described in conjunction with the aforementioned biosensor 1 (refer to FIGS. 3 and 4), for example, as shown in FIGS. 11A to 11C.

According to the present invention, the slit for defining the effective area of the reactive electrode is not necessarily formed in a shape combined by straight lines, and, for example, may be formed of a shape having a curve. In addition, the effective area of the reactive electrode may be defined by other elements than the slit.

The present invention is also applicable to the biosensor obtained by omitting the covers 12 and 42.

Example 1

In this example, the effect obtained when the slit for controlling the effective area of the reactive electrode is provided was evaluated based on a deviation in the area of the reactive electrode.

(Manufacturing of Biosensor)

As the biosensor, two kinds of samples were manufactured, including an original sample having the shape shown in FIGS. 1 to 4 and a comparison sample which does not have the slit for controlling the effective area of the reactive electrode. The electrode of the biosensor was formed to have a width of 0.85 mm and a length of 30 mm by sputtering nickel as a conductive layer on a PET substrate and forming a separation slit having a width of 150 μm using a laser oscillator. The slit for controlling the effective area of the reactive electrode was formed in a U-shape and a rectangular shape having a width of 150 μm using a laser oscillator in a similar way to the case where the separation slit is formed. In the main line of the separation slit, the length was set to 0.65 mm, and the distance was set to 0.65 mm. The shortest distance between the subsidiary line and the cutting slit was set to 0.2 mm.

Meanwhile, the spacer is arranged such that the distance in a longitudinal direction of the substrate becomes 1.4 mm. In the original sample, the target effective area of the reactive electrode was set to 0.7 mm². In the comparison sample, the target area of the reactive electrode was set to 1.2 mm².

The reagent layer containing [Ru(NH$_3$)Cl$_3$] of 20 μg as an electron carrier material and glucose oxidase of 1 unit as the oxidoreductase for a single sensor was formed to cover the reactive electrode and the counter electrode.

(Measurement of Area of Reactive Electrode)

The area of the reactive electrode was measured by capturing an image of the reactive electrode using an image-capturing apparatus for the biosensor before the reagent layer and the cover are formed and processing the obtained image using measurement software known in the art. The result of the measurement for the area of the reactive electrode is shown in the following Table 1.

TABLE 1

| No. | Original Sensor Area of Reactive Electrode [mm²] | Comparison Sensor Area of Reactive Electrode [mm²] |
|---|---|---|
| 1 | 0.684 | 1.138 |
| 2 | 0.698 | 1.154 |
| 3 | 0.689 | 1.146 |
| 4 | 0.702 | 1.162 |
| 5 | 0.678 | 1.154 |
| 6 | 0.681 | 1.174 |
| 7 | 0.675 | 1.161 |
| 8 | 0.685 | 1.172 |
| 9 | 0.685 | 1.151 |
| 10 | 0.683 | 1.159 |
| 11 | 0.683 | 1.134 |
| 12 | 0.685 | 1.152 |
| 13 | 0.681 | 1.130 |
| 14 | 0.691 | 1.139 |
| 15 | 0.672 | 1.111 |
| 16 | 0.682 | 1.142 |
| 17 | 0.673 | 1.097 |
| 18 | 0.677 | 1.121 |
| 19 | 0.669 | 1.096 |
| 20 | 0.672 | 1.116 |
| 21 | 0.660 | 1.123 |
| 22 | 0.672 | 1.136 |
| 23 | 0.675 | 1.164 |
| 24 | 0.674 | 1.191 |
| 25 | 0.675 | 1.187 |
| 26 | 0.688 | 1.205 |
| 27 | 0.680 | 1.204 |
| 28 | 0.684 | 1.225 |
| 29 | 0.678 | 1.215 |
| 30 | 0.684 | 1.229 |
| Ave | 0.681 | 1.156 |
| SD | 0.009 | 0.036 |
| CV % | 1.252 | 3.077 |

As recognized from Table 1, in the original sample, both of the S.D. and the C.V. are smaller, and a deviation in the area of the reactive electrode is smaller in comparison with the comparison sample. Therefore, in the original sample having a slit for controlling the effective area of the reactive electrode, it is possible to form the reactive electrode in a targeted area with excellent accuracy.

Example 2

In this example, the effect obtained when the slit for controlling the effective area of the reactive electrode is provided was evaluated based on deviations in the sensitivity of the sensor and the area of the reactive electrode.

As the biosensor, an original sensor and a comparison sensor were manufactured in a similar way to Example 1.

The sensitivity of the biosensor was evaluated based on the response electric current value measured by supplying a specimen having a glucose concentration of 120 mg/dL to the biosensor. As the response electric current value, a value obtained 5 seconds later after recognizing that the specimen is supplied to the biosensor was employed. The measurement results of the response electric current value are shown in the following Table 2 and FIGS. 15A and 15B in association with the measurement results for the area of the reactive electrode.

TABLE 2

| | Original Sensor | | Comparison Sensor | |
|---|---|---|---|---|
| No. | Area of Reactive Electrode [mm²] | Response Electric Current Value [μA] | Area of Reactive Electrode [mm²] | Response Electric Current Value [μA] |
| 1 | 0.657 | 2.073 | 1.195 | 3.265 |
| 2 | 0.668 | 2.133 | 1.220 | 3.359 |
| 3 | 0.685 | 2.166 | 1.214 | 3.419 |
| 4 | 0.692 | 2.131 | 1.199 | 3.338 |
| 5 | 0.689 | 2.178 | 1.207 | 3.326 |
| 6 | 0.667 | 2.134 | 1.201 | 3.135 |
| 7 | 0.666 | 2.167 | 1.180 | 3.182 |
| 8 | 0.664 | 2.232 | 1.150 | 3.190 |
| 9 | 0.677 | 2.144 | 1.131 | 3.243 |
| 10 | 0.671 | 2.195 | 1.095 | 2.992 |
| 11 | 0.675 | 2.162 | 1.082 | 3.069 |
| 12 | 0.673 | 2.195 | 1.069 | 2.964 |
| 13 | 0.679 | 2.179 | 1.075 | 3.039 |
| 14 | 0.682 | 2.049 | 1.046 | 3.003 |
| 15 | 0.691 | 2.075 | 1.080 | 3.046 |
| Ave | 0.676 | 2.148 | 1.143 | 3.171 |
| SD | 0.011 | 0.051 | 0.063 | 0.149 |
| CV % | 1.563 | 2.358 | 5.501 | 4.701 |

As recognized from Table 2, and FIGS. 15A and 15B, in of the original sample, both of the S.D. and the C.V. are smaller, and a deviation in the area of the reactive electrode and a deviation in the response electric current value (sensitivity) are smaller in comparison with the comparison sample. Therefore, in the original sample having the slit for controlling the effective area of the reactive electrode, it is possible to form the reactive electrode in a targeted area with excellent accuracy and improve the measurement accuracy by suppressing a deviation in the output (response electric current value) of the sensor.

The invention claimed is:

1. A method of manufacturing an analysis tool, the method comprising:
    a first process for forming a plurality of electrodes on a mother substrate, the plurality of electrodes including at least a reactive electrode and a counter electrode;
    a second process for forming an element for defining an effective area for performing transfer of electrons at at least one of the reactive electrode or the counter electrode;
    a third process for defining a contact area that contacts a specimen at the reactive electrode; and
    a fourth process for disposing a reagent layer on the plurality of electrodes, where the reagent layer is constrained within the contact area.

2. The method according to claim 1, wherein the second process includes forming the element for defining the effective area for performing transfer of electrons at the reactive electrode.

3. The method according to claim 1, wherein the second process includes forming a slit in the reactive electrode.

4. The method according to claim 3, wherein the second process includes irradiating laser light onto the reactive electrode.

5. The method according to claim 3, wherein the slit is formed to have a main line extending in a first direction in which the reactive electrode and the counter electrode are aligned and a subsidiary line extending in a second direction that intersects the first direction.

6. The method according to claim 3, wherein the third process includes arranging a control element on the mother substrate and the plurality of electrodes.

7. The method according to claim 6, wherein the control element is arranged such that an edge for controlling the contact area traverses a subsidiary line of the slit.

8. The method according to claim 4, wherein the first process includes irradiating laser light onto a conductive layer after the conductive layer is formed on the mother substrate.

9. The method according to claim 1, wherein the plurality of electrodes includes a plurality of interdigitated reactive electrodes and counter electrodes.

10. The method according to claim 9, wherein the second process includes forming an element for defining an effective area for performing transfer of electrons at a plurality of reactive electrodes.

11. The method according to claim 10, wherein the third process includes defining a contact area that contacts a specimen at the plurality of reactive electrodes.

12. The method according to claim 11, comprising a fifth process including, separating the plurality of electrodes on the mother substrate into a plurality of analysis tools, individual analysis tools comprising a single reactive electrode and a single counter electrode.

13. The method according to claim 1, wherein the third process includes arranging a plurality of control elements on the mother substrate and the plurality of electrodes, the plurality of control elements defining edges of the contact area across the plurality of electrodes.

14. The method according to claim 13, wherein the reagent layer covers the reactive electrode and the counter electrode within the contact area.

15. The method according to claim 5, wherein the slit comprises the main line extending from a first edge of the reactive electrode to the subsidiary line and a second main line extending from the subsidiary line to the first edge of the reactive electrode.

16. The method according to claim 5, wherein the second process includes forming a second slit in the reactive electrode, the second slit extending in the first direction across a width of the reactive electrode.

* * * * *